United States Patent [19]

Farooq

[11] Patent Number: 5,124,417
[45] Date of Patent: Jun. 23, 1992

[54] INITIATORS FOR CATIONIC POLYMERIZATION

[75] Inventor: Omar Farooq, Woodbury, Minn.

[73] Assignee: Minnesota Mining and Manufacturing Company, Saint Paul, Minn.

[21] Appl. No.: 753,987

[22] Filed: Sep. 3, 1991

Related U.S. Application Data

[62] Division of Ser. No. 478,939, Feb. 12, 1990, Pat. No. 5,084,586.

[51] Int. Cl.$^5$ .................................................. C08F 4/06
[52] U.S. Cl. ........................................ 526/90; 526/270; 526/313; 526/315; 526/332; 528/233; 528/234; 528/235; 528/236; 528/237; 528/238; 528/242; 528/409; 528/410; 528/411; 528/412; 528/416
[58] Field of Search ................... 526/90; 528/233, 234, 528/235, 236, 237, 238, 242, 409, 410, 411, 412, 416

[56] References Cited

U.S. PATENT DOCUMENTS

| 4,472,268 | 9/1984 | Olah | 208/134 |
| 4,547,474 | 10/1985 | Olah | 502/168 |
| 4,721,559 | 1/1988 | Olah | 208/135 |

OTHER PUBLICATIONS

H. Meerwein, "Triethyloxonium Fluoborate", *Org. Synth.*, coll. Vol. V, pp. 1080-1083, 1096-1099.
Mellela et al., *Can. J. Chem.*, 1987, vol. 65, p. 2649.
R. Dalziel and F. Aubke, "Trifluoromethanesulfonate of Iodine", *Inorg. Chem.*, 1973, vol. 12, p. 2707.
R. Miethchen, *Z. Chem.*, 1986, vol. 26, p. 168.

*Primary Examiner*—Joseph L. Schofer
*Assistant Examiner*—N. Sarofim
*Attorney, Agent, or Firm*—Gary L. Griswold; Walter N. Kirn; Gregory A. Evearitt

[57] ABSTRACT

Disclosed are novel compounds which are useful as initiators for cationically polymerizable monomers. The novel compounds comprise a carbon containing cation (e.g., trimethyloxonium) which is capable of initiating cationic polymerization and a non-nucleophilic counterion which is an at least partially fluorinated hydrocarbylsulfonato metallate (e.g. perfluoroethylsulfonato-aluminate). The disclosed initiators are capable of initiating the cationic polymerization of a wide variety of monomers such as epoxides, tetrahydrofuans, oxazolines, vinyls, lactones, and the like.

11 Claims, No Drawings

INITIATORS FOR CATIONIC POLYMERIZATION

This is a division of application filed Feb. 12, 1990 now U.S. Pat. No. 5,084,586.

BACKGROUND OF THE INVENTION

1. Field of the Invention

This invention relates to novel salt compounds containing onium cations and non-nucleophilic complex metallate anions and more particularly, it relates to anions with at least partially fluorinated ligand coordinated to the metal. It also relates to the use of the compounds as novel initiators for the cationic polymerization of various monomers.

2. Background of the Art

Iodonium, oxonium, sulfonium, sulfoxonium, and various other onium salts are well known in the art, particularly as initiators of cationic and free radical polymerization. The effectiveness of these onium salts as initiators in cationic polymerizations, and particularly in achieving high molecular weight polymers, is known to be greatly influenced by the nucleophilic nature of the anion employed in the salt. Generally, non-nucleophilic anions function much better than their nucleophilic counterparts. This is because strong nucleophilic anions have a much greater tendency to terminate the polymer chain than do non-nucleophilic anions.

Examples of nucleophilic anions which are recognized as being detrimental counterions include fluoride, chloride, bromide, iodide, bisulfide, cyanide, bicarbonate, carbonate, nitrate, hydroxide, carboxylates, sulfonates, and trifluoromethanesulfonate (also referred to commonly as "triflate").

Examples of non-nucleophilic anions include hexafluorophosphate $(1-)$, hexafluoroarsenate $(1-)$, tetrafluoroborate $(1-)$, hexafluoroantimonate $(1-)$, tetraphenylborate $(1-)$, and perchlorate. The use of such non-nucleophilic ions as counterions for nucleophilic sensitive cations is known, e.g., triethyloxonium tetrafluoroborate is a known stable complex. (see Meerwein, H. *Org. Syn.* Coll. Vol. V, 1080, 1096.

Triflate species, when paired with various materials, have been used as counterions. For example, the trifluoromethanesulfonate substituted tin centered anion is known as a counterion in organometallic complexes involving the $+4$ oxidation state of tin (see Mallela, et al., *Can. J. Chem.* 1987, 65, 2649). By further way of example, tetrakis(trifluoromethanesulfonato)iodate $(1-)$ anion has been prepared as salts with alkali metals (see Dalziel, J. R.; Aubke, F., *Inorg. Chem.* 1973, 12, 2707) and tetrakis(trifluoromethanesulfonato)boric acid is known in the art for use in Friedel-Crafts alkylations (see Miethchen, R. et al., *Z. Chem.* 1986, 26, 168).

U.S. Pat. No. 4,721,559 discloses the use of boron, aluminum, and gallium perfluoroalkane sulfonates as Friedel-Crafts catalysts.

U.S. Pat. No. 4,547,474 discloses the use of $C_{10}$ to $C_{18}$ perfluorinated alkanesulfonic acid based superacidic catalysts in various hydrocarbon conversion processes.

U.S. Pat. No. 4,472,268 discloses a process for upgrading natural gasoline by treatment with a liquid ternary catalyst system comprising trifluoromethanesulfonic acid and hydrogen fluoride in conjunction with a Lewis Acid catalyst of the formula $MX_n$ where M is selected from Groups IIIA, IVB, or V elements of the Periodic Table, X is halogen, and n is a number varying from 3 to 6.

SUMMARY OF THE INVENTION

The present invention provides an effective initiator for the cationic polymerization of a wide variety of cationically polymerizable monomers. Also provided is a process using the initiators of this invention in cationic polymerization reactions.

Briefly, the inventive initiator comprises an onium cation which is effective in the cationic polymerization of various monomers and a non-nucleophilic anion which does not interfere with cationic polymerizaton reactions. The inventive initiator comprises a compound which may be represented by the following formula:

wherein:

Y is a cation selected from the group consisting of oxonium, sulfonium, sulfoxonium, selenonium, iodonium, diazonium, pyrylium, carbenium, and acylium cations;

R is independently selected from the group consisting of:

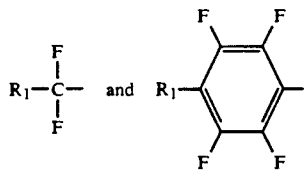

$R_1$ is hydrogen, halogen, an alkyl group or an aryl group;

F is fluorine;

M is an element chosen from Groups 3-15, inclusive, of the Periodic table; z is 1, 2, 3, or 4; and a, b, and n are integers with the proviso $z \leq n$ and that integer a multiplied by integer b equals z.

The novel polymerization process of the present invention comprises intimately contacting a cationically polymerizable monomer with a cationic polymerization initiator of the formula

as defined above, thereby initiating polymerization of said monomer. Preferably, the intimate contacting is done in solution. Generally, the mere intimate contacting of the initiator and monomer will be sufficient to effect initiation of cationic polymerization. However, it will be preferable in some cases, depending upon the type of initiator, to help induce initiation or accelerate the reaction through the use of heat or actinic radiation.

COMPARISON TO THE PRIOR ART

Various types of perfluorosulfonato-containing compounds are known in the prior art and have been used as counterion ions with simple cations, e.g., potassium iodine tetrakis(trifluoromethanesulfonate)iodate $(1-)$ (see Dalziel, J. R.; Aubke, F. *Inorg. Chem.* 1973, 12, 2707). The initiators of the present invention differ because the cationic species is an alkyl or aryl substituted non-metallic cation and not an alkali metal like potassium and additionally, iodine is not within the scope of anion of the present invention. The foregoing reference also makes no mention of using the potassium salt of iodine triflate in hydrocarbon conversion reactions.

S. R. Mallela et al. disclosed the existence of a series of hetero-bimetallic fluorosulfonate bridged coordination polymers of the type $M(II)Sn(SO_3F)_6$ wherein $M(II)=Mn$, Fe, Co, Ni, or Cu (see Mallela, S. P. et al., Can. J. Chem. 1987, 65, 2649). The present invention differs from this reference because the cation in the present invention is alkyl- or aryl-substituted and the anion contains alkyl or aryl groups, the presence of which in the anion help to prevent the termination of the polymer chain by a strong nucleophile such as fluorine. No disclosure is given by the reference for use of the disclosed coordination polymer in any hydrocarbon conversion reactions such as cationic polymerizaton.

The perfluoroalkanesulfonates of boron, aluminum, and gallium, disclosed in U.S. Pat. No. 4,721,559 are all charge neutral species unlike the negatively charged anionic species of the present invention.

The perfluorinated alkanesulfonic acids disclosed in U.S. Pat. No. 4,547,474 are conventional protic acids containing an anion with no metallic substance. Furthermore, the sulfonic acids are all absorbed on supports, such as silica, to which Lewis acids are bonded. The present invention does not require supports to absorb the cation and anion of the initiator.

Unlike the prior art, the present invention pertains to certain alkyl or aryl substituted onium cations in combination with at least partially fluorinated alkanesulfanatometallate counterions. A particularly effective cationic polymerization initiator is achieved because the onium cations are all effective initiators of cationic polymerization and the at least partially fluorinated counterions employed are all non-nucleophilic and therefore serve to terminate the polymerization reaction less than conventional, prior art polymerization terminators do. Consequently, as will be seen by the examples later herein, the inventive polymerization initiators help produce higher molecular weight polymers.

DETAILED DESCRIPTION OF THE INVENTION

The novel cationic polymerization initiators of the present invention may be represented by the formula:

$$Y_a{}^{b+}[(RSO_3)_nM)]_c{}^{d-}$$

wherein: Y is a cation selected from the group consisting of oxonium, sulfonium, sulfoxonium, selenonium, iodonium, diazonium, pyrylium, carbenium, and acylium cations.

Non-limiting examples of these cations include, but are not limited to: trialkyloxonium, preferably trialkyloxonium having from 3 to 54 carbon atoms (e.g., trimethyloxonium, triethyloxonium, trihexyloxonium, trioctadecyloxonium, etc.); alkyldiaryloxonium, preferably alkyldiaryloxonium having from 8 to 60 carbon atoms (e.g., dimethylphenyloxonium, octylmethylnaphthyloxonium, etc.); aryldialkyloxonium, preferably aryldialkyloxonium having from 14 to 48 carbon atoms; triaryloxonium, preferably triaryloxonium having from 18 to 45 carbon atoms (e.g., triphenyloxonium, diphenyl(naphthyl)oxonium, etc.); trialkylsufonium, preferably trialkylsufonium having from 3 to 54 carbon atoms (e.g., trimethylsulfonium, tributylsufonium, dimethylethylsulfonium, etc.); alkyldiarysulfonium, preferably alkyldiarylsulfonium having from 8 to 60 carbon atoms (e.g., diphenylmethylsulfonium, ethylphenylnaphthylsulfonium, etc.); aryldialkylsulfonium, preferably aryldialkylsufonium having from 14 to 48 carbon atoms (e.g., diethylphenylsulfonium, ethyloctadecylphenylsulfonium, etc.); triarylsulfonium, preferably triarylsulfonium having from 18 to 45 carbon atoms (e.g., triphenysulfonium, diphenylnaphthylsulfonium, etc.); trialkylsufoxonium, preferably trialkylsulfoxonium having from 3 to 54 carbon atoms (e.g., trimethylsulfoxonium, tributylsulfoxonium, dimethylethylsulfoxonium, etc.); alkyldiarylsulfoxonium, preferably alkyldiarylsulfoxonium having from 8 to 60 carbon atoms (e.g., diphenylmethylsulfoxonium, ethylphenylnaphthylsulfoxonium, etc.); aryldialkylsulfoxonium, preferably aryldialkylsulfoxonium having from 14 to 48 carbon atoms (e.g., diethylphenylsulfoxonium, ethyloctadecylphenylsulfoxonium, etc.); triarylsulfoxonium, preferably triarylsulfoxonium having from 18 to 45 carbon atoms (e.g., triphenylsulfonium, diphenylnaphthylsulfonium, etc.); trialkylselenoium, preferably trialkylselenonium having from 3 to 54 carbon atoms (e.g., trimethylselenonium, triethylselenonium, trihexylselenonium, trioctadecylselenonium, etc.); alkyldiaryselenonium, preferably alkyldiarylselenonium having from 8 to 60 carbon atoms (e.g., dimethylphenylselenoium, octylmethylnaphthylselenonium, etc.); aryldialkylselenonium, preferably aryldialkylselenonium having from 14 to 48 carbon atoms (e.g., triarylselenonium, preferably triarylselenonium having from 18 to 45 carbon atoms (e.g., triphenylselenonium, diphenyl(naphthyl)selenonium, etc.); dialkyliodonium, preferably dialkyliodonium having from 2 to 36 carbon atoms (e.g., dimethyliodonium, hexylpropyliodonium, diocatdecylodonium, etc.); alkylaryliodonium, preferably alkylaryliodonium having from 7 to 35 carbon atoms (e.g., methylphenyliodonium, ethylphenyliodonium, etc.); alkynylaryliodonium, preferably alkynylaryliodonium having from 8 to 33 carbon atoms (e.g., phenyl(phenylethynyl)iodonium, naphthyl(phenylethynyl)iodonium, etc.); diaryliodonium, preferably diaryliodonium having 12 to 30 carbon atoms (e.g., diphenyliodonium, naphthylphenyliodonium, etc.); alkyldiazonium, preferably alkyldiazonium having from 1 to 18 carbon atoms (e.g., methyldiazonium, hexyldiazonium, etc.); aryldiazonium, preferably aryldiazonium having from 6 to 15 carbon atoms(e.g., phenyldiazonium, naphthyldiazonium, etc.); alkylacylium, preferably alkylacylium having from 2 to 19 carbon atoms (e.g., acetylium, butylium, decylium, etc.); arylacylium, preferably arylacylium having from 7 to 16 carbon atoms (e.g., benzoylium, naphtoylium, etc.); triarylcarbenium such as triphenylcarbenium (i.e., trityl), etc; and pyrylium, preferably pyrylium having from 5 to 50 carbon atoms. The substituents on the oxonium, sulfonium, sulfoxonium, and iodonium cations may either be individually distinct or be connected to each other so as to form one or more rings, including aromatic rings, containing the heteroatom O, S, or I.

The onium cations employed in the present invention are prepared by those methods which are well known to those skilled in the art. Typically in the same reaction that the onium cation is formed, an anionic (counterion) species will also be formed and thus an onium salt is created in the overall process. For example, trialkyloxonium salts with perhalogenated complex anions are generally prepared by alkylation of dialkyl ethers using alkyl halides as alkylating agents in the presence of strong halide acceptors such as halogenated Lewis acids (Perst, H. Carbonium Ions; Olah, G. A.; Schleyer, P. v.

R., Eds.; John Wiley & Sons, New York, 1976 1961-2047). Additionally, oxonium salts may also be prepared by using perfluoroalkanesulfonated Lewis acid-ether adducts in the presence of epichlorohydrin via the intermediacy of an inner oxonium salt similar to procedures known in the art to incorporate the perfluorinated anions in the oxonium salts (see Meerwein, H.; Battenberg, E.; Gold, H.; Pfeil, E.; William, G. *J. Prakt. Chem.* 1939, 154, 83; Meerwein, H.; Hinz, G.; Hoffman, P.; Kronig, E.; Pfril, E. *J. Prakt. Chem.*, 1937, 147, 257; and Meerwein, H. *Org. Synth.* 1966, 46, 113).

Trialkyloxonium salts of the present invention may also be prepared by using secondary oxonium ion salts with a per(perfluoroalkanesulfonated) complex anion using diazo alkanes similar to the procedure known in the art for the preparation of certain perfluorinated oxonium salts (see Klages, F.; Meuresch, H. *Chem. Ber.* 1952, 85, 863; and Klages, F.; Meuresch, H.; Steppich, W. *Ann. Chem. Liebigs.* 1955, 592, 116). Furthermore, disproportionation of the perfluoroalkanesulfonated strong Lewis acid-ether adducts also gives oxonium salts similar to those described herein (see Goodrich, R. A.; Treichel, P. M. *J. Am. Chem. Soc.* 1966, 88, 3509). Oxonium salts of the present invention are also prepared using trans-alkylation reactions. Thus, trimethyloxonium tetrakis(trifluoromethanesulfonato)aluminate was prepared using triethyloxonium tetrakis(trifluoromethanesulfonato)aluminate in dimethyl ether in respectable yield.

Diaryliodonium salts of the present invention can be prepared by the action of diaryliodonium perfluoroalkanesulfonates on appropriate perfluoroalkanated Lewis acids (e.g., diaryliodonium tetrakis(trifluoromethanesulfonato)borate(131)), or by the action of diaryliodonium perfluoroalkanesulfonates on appropriate halogenated lewis acids followed by removal of halides using required amounts of perfluoroalkanesulfonic acid. In lieu of diaryliodonium perfluoroalkanesulfonates, the corresponding halides or pseudohalides can be employed with perfluoroalkanesulfoated or halogenated Lewis acids followed by a stoichiometric amount of perfluoroalkanesulfonic acid. Diaryliodnium salts of the present invention are also conveniently prepared using the corresponding halides with appropriate metal salts of a per(perfluoroalkanesulfonated) complex anion (e.g., coinage and alkali metal salts as exemplified by the preparation of diphenliodonium tetrakis(trifluoromethanesulfonato)borate(1−) using silver tetrakis(trifluoromethanesulfonato)borate(1−)). This procedure is similar to those known in the art viz. use of alkali metal salts with perfluorinated anions (see Crivello, J. V.; Lam, H. W. *J. Polym. Sci. Symp.* 1976, 36, 383; and U.S. Pat. Nos. 4,151,175; 4,238,394; 4,683,317; 4,529,490 to Crivello). Metal salts of per(perfluoroalkanesulfonated) complex anions used in the preparation of said iodonium salts may conveniently be replaced by conjugate Brønsted Lewis superacids having same type of complex anion similar to procedures known in the art (Pappas, S. P.; Pappas, B. C.; Gatechair, L. R. *J. Polym. Sci., Polym. Chem. Ed.* 1984, 22, 69).

The procedures outlined for the preparation of diaryliodonium salts may equally be applied to that of triarylsulfonium salts of the present invention. The sulfonium salts, however, may also be prepared by the action of a diaryliodonium salt/per(perfluoroalkanesulfonated) complex anion on a diarysulfide using a copper salt as catalyst (see Crivello, J. V.; Lam, H. W. *J. Polym. Sci., Polym. Chem. Ed.* 1979, 17, 977.

The non-nucleophilic anion of the cationic polymerizaton initiator of the present invention is described by the formula:

$$[(RSO_3)_nM]^{z-}$$

and serves as a counterion to the cationic species $Y_a^{b+}$.

In the foregoing formula each R is independently selected from the group consisting of:

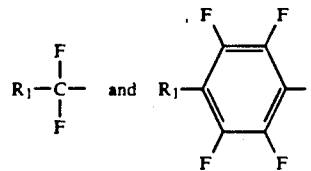

wherein $R_1$ represents either hydrogen, halogen, an alkyl group or an aryl group and F is fluorine. Preferably, each R will individually represent a perfluorinated alkyl radical or a perfluorinated aryl radical and most preferably, a $C_1-C_{10}$ perfluorinated alkyl radical.

M is an element chosen from Groups 3–15, inclusive, of the Periodic Table as depicted in *Chemical and Engineering News* 1985, 63, 26. Preferably M is an element chosen from Groups 4–14 of the Periodic Table, and more preferably is chosen from the group of B, Al, Ga, Sn, Fe, Zr, Hf, Nb, and Ta.

In the foregoing formula, z is 1, 2, 3, or 4 and a, b, and n are integers such that z is less than or equal to n and the product of integer a multiplied by integer b equals z.

As is well understood in this technical area, a large degree of substitution is not only tolerated, but is often advisable. As a means of simplifying the discussion and recitation of these groups, the terms "group" and "radical" are used to differentiate between chemical species that allow for substitution or which may be substituted. For example, the phrase "alkyl group" is intended to include not only pure hydrocarbon alkyl chains such as methyl, ethyl, octyl, cyclohexyl, isoctyl, tert-butyl and the like, but also such alkyl chains bearing such conventional substituents in the art such as hydroxyl, alkoxy, phenyl, halo (F, Cl, Br, I), cyano, nitro, amino, etc. The phrase "alkyl radical" on the other hand is limited to the inclusion of only pure hydrocarbon alkyl chains such as methyl, ethyl, propyl, cyclohexyl, isooctyl, tert-butyl, and the like.

Although the anion of the present invention can be formed in the same reaction with the onium cation thereby creating onium salt as described earlier herein, there may be instances, as will be seen by the Examples, where it is appropriate to synthesize the anionic species separately and then combine it with an onium cation that has been separated from an onium salt.

Thus, perfluoroalkanesulfonated complex anions of the present invention can themselves be prepared by one or more of the following general procedures:

(1) Reaction of a perfluoroalkanesulfonated strong Lewis acid with a perfluoroalkanesulfonated precursor. Suitable precursors include, but are not limited to, alkali metal and alkaline earth metal perfluoroalkanesulfonates; ammonium and phosphonium, including alkyl and aryl substituted ammonium and phosphonium, perfluoroalkanesulfonates; alkyl perfluoroalkanesulfonates; pyridinium and substituted pyridinium perfluoroalkanesulfonates.

(2) Removal of halides (e.g., F-, Cl-, Br-, I-) or pseudo-halides (i.e., strongly electron withdrawing groups such as cyano, nitrosyl, thiocyanato, and the like) from a perhalogenated or per(pseudohalogenated) or mixed halogenated-perfluoroalkanesulfonated complex anion by stoichiometric amounts of perfluoroalkanesulfonic acids at subzero or higher temperature depending on the reactivity of the anion toward acids used. Removal of halide from the corresponding complex anion may also be effected by using coinage or alkali metal perfluoroalkanesulfonates (e.g., silver triflate) to cause the precipitation of metal halides.

(3) Removal of alkyls, aryls, halides or pseudo-halides from a peralkylated, perarylated, peralkarylated, mixed alkyl-halogenated, mixed aryl-halogenated or mixed pseudo-halogenated complex anion by using appropriate equivalents of perfluoroalkanesulfonic acid under conditions mentioned in (2). Because formation of alkanes or arenes by the action of acid is a highly favorable irreversible thermodynamic process, it may result in ready preparation of the complex anions of present invention. Many metal alkyls are extremely reactive even to weak acids (e.g., alcohols (see Mole, T.; Jeffery, E. A. *Organoaluminum Compounds;* Elsevier: New York, 1972); Giannini, U.; Zucchini, U.: Albizzati, E.; D'Angelo, R. *Chem. Comm.*, 1969, 1174; Giannini, U.; Zucchini, U, *Chem. Co,* 1968, 940; Pedley, J. B.; Marshal, E. M. *J. Phys. Chem. Ref. Data.* 1984, 12, 967; Smoes, S.; Myers, C. E.; Drowart *J. Chem. Phys. Lett.* 1971, 8, 10; Gupta, S. K.; Gingerich, K. A. *J. Chem. Phys.* 1981, 74, 3584; Stearns, C. A.; Kohl, F. J. *High Temp. Sci.* 1974, 6, 284).

Suitable monomers for polymerization by the initiators of the present invention are those which can be polymerized cationically through initiation by an alkyl, or aryl containing cation; examples include, but are not limited to, cyclic ethers such as epoxides (e.g., styrene oxide, vinylcycohexene dioxide, glycidylmethactylate, ethylene oxide, epichlorohydrin, etc.), oxetanes (e.g., oxetane, phenyloxetane, etc.), tetrahydrofurans (e.g., tetrahydrofuran, 2-methyltetrahydrofuran, etc.), tetrahydropyrans (tetrahydropyran, 3-propyltetrahydropyran, etc.), etc.; alkenyl monomers such as styrene and its homologs, alkenylfurans, conjugated dienes (e.g., cyclopentadiene, 2,4-hexadiene, etc.), isobutylene, vinyl ethers (e.g., methyl vinyl ether, ethyl vinyl either, octadecyl vinyl ether, phenyl vinyl ether, etc.) including fluorinated vinyl ethers; lactones (e.g., $\beta$-propiolactone, $\gamma$-butyrolactone, $\delta$-caprolactone, etc.); oxazolines (e.g., oxazoline, 2-phenyloxazoline, 2-decyloxazoline, etc.); aziridines (e.g., aziridine, N-ethylaziridine, etc.); cyclosiloxanes (e.g., hexamethyltrisloxanes, octamethylcyclotetrasiloxane, triphenyltrimethylcyclotrisiloxane, etc.); ketals (e.g., 1,3-dioxolane, 1,3-dioxane, 2,2-dimethyl-1,3-dioxane, 2-phenyl-1,3-dioxane, 2,2-dioxolane-1,3-dioxolane, etc.); cyclic anhydrides (e.g., phthalic anhydride, maleic anhydride, succinic anhydride, etc.); lactams (e.g., $\beta$-propiolactam, $\gamma$-butyrolactam, $\delta$-caprolactam, etc.); and aryl dialdehydes (e.g., 1,2-benzenedicarboxaldehyde, 1,3-benzenedicarboxaldehyde, 1,2-naphthalenedialdehyde, etc.).

The monomer and cationic polymerization initiator should be brought into intimate contact with one another in order to initiate polymerization. As used herein, "intimate contact" between the initiator and the monomer occurs when the two are brought into such direct or close physical contact that one or more cationic groups which initiate polymerization are transferred from the initiator to the monomer. Typically this is done in solution. In some instances, depending upon the type of cationic initiator used, it will be preferable to use heat or actinic radiation to induce initiation of polymerization or increase its rate. The auxiliary conditions used in conjunction with certain cations is well known in the art, such as, for example, the use of heat in conjunction with oxonium cations and the use of actinic radiation and a photosensitizer in conjunction with iodonium cations.

Conditions for cationic polymerization of monomers is well known in the art. For example, it is desirable to have essentially anhydrous solution conditions. It is also desirable to have high purity monomers. In order to effect many cationic polymerizations, it is necessary to supply a source of heat. In the case of photoinitiators, it is necessary to expose the photoinitiator to actinic radiation.

The following non-limiting examples further illustrate the present invention.

EXAMPLES

The materials prepared in the following examples were analyzed by one or more of the following techniques and gave results consistent with the assigned identities: $^1H$, $^{27}Al$, $^{13}C$, $^{11}B$ nuclear magnetic resonance, melting point, elemental analysis, mass spectroscopy, infrared spectroscopy, and in the case of polymers gel permeation chromatography.

All materials were obtained from Aldrich Chemical Company (Milwaukee, Wis.) unless otherwise indicated.

EXAMPLE 1

This example describes the preparation of triethyloxonium tetrakis(trifluoromethanesulfonato)aluminate (1—).

To a well stirred slurry of 4.2 g (8.86 mmol) aluminum trifluoromethanesulfonate in 40 ml dry ether in a Schlenk flask under dry argon was added 4.6 ml (36 mmol) ethyl trifluoromethanesulfonate. The mixture was refluxed for about 20 hr during which a beige precipitate formed. The supernatant solution was removed and fresh ether was added to restore the original volume, and the mixture was refluxed under argon an additional hour. The procedure was repeated 4 times and finally the ether was removed and the beige solid dried in vacuo at 5°-100° C. for 2 hours to isolate the oxonium salt, 5.6 g (88% yield).

EXAMPLE 2

This example describes the preparation of triethyloxonium tetrakis(trifluoromethanesulfonateo)gallate (1-).

The procedure of example 1 was followed using 4.59 g gallium trifluoromethanesulfonate in place of the aluminum trifluoromethansulfonate. The oxonium salt, 5.5 g was obtained (81% yield).

EXAMPLE 3

This example describes the preparation of trimethyloxonium tetrakis(trifluoromethanesulfonate)aluminate (1-).

In a dry box 2.1 g (4.43 mmol) aluminum trifluoromethanesulfonate and 2 ml (18 mmol) methyl trifluoromethanesulfonate were added to 30 ml dry 1,1,2-trichlorotrifluoroethane in an autoclave equipped with a magnetic stirrer. About 30 g dimethyl ether was condensed into the autoclave by application of a low temperature bath. After sealing the autoclave was heated to 40° C. for 8-12 hr. The autoclave was cooled to room temperature and slowly discharged. The beige solid was transferred to a Schlenk flask in the dry box and washed several times with dry 1,1,2-trichlorotrifluoroethane and finally dried in vacuo at 50° C. for 2 hr, 2.6 g (90% yield).

EXAMPLE 4

This example describes the preparation of trimethyloxonium tetrakis(trifluoromethanesulfonato)gallate (1-).

According to the procedure of example 3, 2.3 g (4.43 mmol) of gallium trifluoromethanesulfonate was employed in place of aluminum trifluoromethanesulfonate to give 2.7 g of product as a solid (84% yield).

EXAMPLE 5

This example describes the preparation of tri-n-propyloxonium tetrakis(trifluoromethanesulfonato)aluminate (1-).

To a well stirred solution of 6.3 g (13.2 mmol) aluminum trifluoromethanesulfonate in 50 ml dry n-propyl ether in a Schlenk flask under dry argon was added 0.8 ml (10 mmol) epichlorohydrin. The mixture was stirred at room temperature for 4 hr. The beige precipitate was washed several times with n-propyl ether and dried in vacuo at 50° C. for 2 hr, 9.0 g (89% yield).

EXAMPLE 6

This example describes the preparation of tri-n-propyloxonium tetrakis(trifluoromethanesulfonato)gallate (1-).

According to the procedure of example 5, 6.9 g (13.3 mmol) gallium trifluoromethanesulfonate was used in place of aluminum trifluoromethanesulfonate to give 9.2 g to product as a solid (85% yield).

EXAMPLE 7

This example describes the preparation of triethylsulfonium tetrakis(trifluoromethanesulfonato)aluminate (1-).

To a well stirred slurry of 2.1 g (4.43 mmol) aluminum trifluoromethanesulfonate in 20 ml dry diethyl sulfide in a Schlenk flask under dry argon and the mixture was refluxed for 6 hr. The supernatant diethyl sulfide was removed and the viscous lower phase was washed several times with diethyl sulfide under reflux, and then dried in vacuo at 50° C. for 3 hr, 3.1 g (94% yield).

EXAMPLE 8

This example describes the preparation of diphenyliodonium tetrakis(trifluoromethanesulfonato)borate (1-).

To a suspension of 2.1 g (4.89 mmol) diphenyliodonium trifluoromethanesulfonate in 20 ml 1,1,2-trichlorotrifluoroethane was added dropwise a solution of 2.2 g (4.8 mmol) boron trifluoromethanesulfonate in 1,1,2-trichlorotrifluoroethane TM. The mixture was stirred under dry argon for 3 hr at room temperature. Diphenyliodonium tetrakis(trifluoro-methanesulfonato)borate was precipitated following dissolution of the precursor. The precipitate was treated with a mixture of anhydrous sodium sulfate and sodium bicarbonate in dry tetrahydrofuran. The tetrahydrofuran solution was filtered, concentrated under reduced pressure and precipitated using hexane, filtered, and dried in vacuo, 4.1 g (95% yield).

EXAMPLE 9

This example describes and alternate preparation of diphenyliodonium tetrakis(trifluoromethanesulfonato)borate (1-).

To a mixture of 1.5 g (4.8 mmol) diphenyliodonium chloride in 20 ml dry nitromethane, was added an equimolar solution of silver tetrakis(trifluoromethanesulfonato)borate in nitromethane was added in one portion at room temperature. After stirring for 2 hrs the precipitated silver chloride was filtered off and the filtrate was dried over anhydrous sodium sulfate-sodium bicarbonate as described in Ex. 8 and then concentrated under reduced pressure. Hexane was added to cause precipitation of the iodonium tetrakis(trifluoromethanesulfonato)borate, 3.9 g (90% yield).

EXAMPLE 10

This example describes the preparation of acetylium tetrakis(trifluoromethanesulfonato)borate(1-).

To a well stirred solution of 6.6 g (9.24 mmol) silver tetrakis(trifluoromethanesulfonate)borate in 20 ml liquid $SO_2$ at $-40°$ C., was added 1.14 g (9.24 mmol) acetyl bromide. Silver bromide precipitated immediately, and the mixture was stirred for an additional 30 min. The solution was quickly filtered through glass wool in a cooled Schlenk flask ($-30°$ C.), and the solvent was removed at this temperature under reduced pressure. Acetylium tetrakis(trifluoromethylsulfonato)borate (1-) was obtained as an off-white solid, 5.0 g (83% yield).

EXAMPLE 11

This example describes the preparation of 2,4,6-trimethylpyrylium tetrakis(trifluoromethanesulfonato)borate (1-).

A solution of 2.3 g (5.1 mmol) boron tris(trifluoromethanesulfonate) in 1,1,2-trichlorotrifluoroethane was added dropwise to a well stirred solution of 1.2 g (5.1 mmol) 2,4,6-trimethylpyrylium trifluoromethanesulfonate (*Org. Syn.*, 4, 1114) in 10 ml chloroform. The mixture was stirred for 30 min and hexane was added and the resultant precipitate was removed by filtration, and dried in vacuo to give 2,4,6-trimethylpyrylium tetrakis(trifluoromethylsulfonato)borate as an off-white solid, 3.0 g (81% yield).

EXAMPLE 12

This example demonstrated the preparation of diphenyliodonium tetrakis(trifluoromethanesulfonato)ferrate (1-).

Diphenyliodonium trifluoromethanesulfonate 2.65 g, (6.1 mmol) was added to a suspension of 1.0 g (6.1 mmol) ferric chloride in 20 ml dry 1,1,2-trichlorotrifluoroethane. The mixture was heated to reflux for 6 hr to obtain diphenyliodonium trichloro(trifluoromethanesulfonato)ferrate as a solid. To said solid 1.62 ml trifluoromethanesulfonic acid was added dropwise and the reaction mixture was further refluxed overnight. The beige solid formed was dissolved in dry nitromethane containing 0.5 g anhydrous sodium sulfate and sodium bicarbonate and the solution was filtered after stirring. Removal of the solvent in vacuo diphenyliodonium tetrakis(trifluoromethanesulfonato)ferrate (1-), 5.2 g (91% yield).

EXAMPLE 13

This example describes the preparation of triethyloxonium hexakis(trifluoromethanesulfonato)stannate (1-).

To a suspension of 3 g (4.2 mmol) tetrakis(trifluoromethanesulfonato)tin in dry ethyl ether under argon was added 3 g (16.8 mmol) ethyl triflate. The mixture was refluxed for 14 hr. The precipitated oxonium slat was washed several times with refluxing dry ether to remove excess ethyl trifluoromethanesulfonate. The resultant solid was dried at about 50° C. and triethyloxonium hexakis(trifluoromethanesulfonate)stannate (2-) was obtained as a white solid, 3.8 g (80% yield).

The following examples demonstrate that the salts of the present invention are useful as initiators for cationic polymerization.

EXAMPLE 14

Polymerization of tetrahydrofuran: Tetrahydrofuran (89 g, 1.2 mol) was distilled from sodium-naphthalene into a dry 250 ml Schlenk flask under argon. Onium salt initiator was added directly from another Schlenk flask under argon with stirring. The solution was stirred for more than 12 hrs at room temperature, at which time the gelled material was completely dissolved in a solution of water/tetrahydrofuran (1:20), using a mechanical stirrer. Addition of methanol precipitated a flocculent solid, which was filtered and dried in vacuo to give polytetramethylene ether. Results are summarized in Table 1.

TABLE 1

| Initiator | [Initiator] mol/ $1 \times 10^3$ | Polymerization Time (hr) | % Yield |
|---|---|---|---|
| $(CH_3CH_2)_3O^+$ $(CF_3SO_3)_4Al^-$ | 5.4 | 20 | 80 |
| $(CH_3CH_2)_3O^+$ $(CF_3SO_3)_4Ga^-$ | 19.9 | 20 | 69 |
| $(CH_3)_3O^+$ $(CF_3SO_3)_4Al^-$ | 7.8 | 18 | 76 |
| $CH_3(C=O)^+$ $(CF_3SO_3)_4B^-$ | 8.1 | 16 | 67 |
| $C_6H_5(C=O)^+$ $(CF_3SO_3)_4B^-$ | 6.7 | 16 | 64 |

EXAMPLE 15

Polymerization of cyclohexane oxide: into a dry 100 ml Schlenk flask under argon, and equipped with a magnetic stirbar, was placed 4 ml dry cyclohexene oxide, 4 ml dry dichloromethane. Onium salt initiator (70 mg) was added at −10° C. with stirring. The mixture was stirred 15 min at a temperature of −10° C., then quenched with aqueous ammonium hydroxide. The polymer was precipitated with methanol and dried in vacuo. Results are shown in Table 2.

TABLE 2

| Initiator | [Initiator] mol/ $1 \times 10^3$ | Polymerization Time (hr) | % Yield |
|---|---|---|---|
| $(CH_3CH_2)_3O^+$ $(CF_3SO_3)_4Al^-$ | 12.8 | 0.25 | 98 |
| $(CH_3CH_2)_3O^+$ $(CF_3SO_3)_4Ga^-$ | 12.0 | 0.5 | 91 |
| $CH_3(C=O)^+$ $(CF_3SO_3)_4B^-$ | 24.1 | 0.25 | 75 |
| $(CH_3CH_2)_3S^+$ $(CF_3SO_3)_4Al^-$ | 19.3 | 168 | 73 |

EXAMPLE 16

Polymerization of α-phthalaldehyde: a solution of 18.7 mg triethyloxonium tetrakis(trifluoromethylsulfonato)aluminate in dry nitromethane was added under argon to a 100 ml Schlenk flask containing 25 ml dry methylene chloride, a magnetic stirbar, and 5.2 g of α-phthalaldehyde cooled to −78° C. The reaction was allowed to continue for 18 hr. Pre-cooled dry pyridine (10 ml) was added to the reaction at −78° C., and the reaction was poured into a mechanically stirred solution of methanol. The precipitated polymer was filtered, washed with methanol, and dried in vacuo, yield 98%. When the above polymerization was carried out using triethyloxonium tetrakis(trifluoromethanesulfonato)gallate as initiator, the yield was 69% in 4 hr.

EXAMPLE 17

Polymerization of β-propiolactone: A solution of 30 mg triethyloxonium tetrakis(trifluoromethanesulfonato)aluminate in 1 ml dry nitromethane was added to a 25 ml Schenk flask cooled to 0° C. under argon and containing 1 g β-propiolactone in 1 ml dry dichloromethane. The reaction was allowed to stand for 18 hr at 0° C., then quenched with a few drops of water. Solvent was removed under reduced pressure and the polymer was precipitated using hexane, filtered, and dried in vacuo, 95% yield. When the above procedure was repeated with tetrakis(trifluoromethanesulfonato)gallate as the initiator, similar results were obtained.

EXAMPLE 18

Polymerization of isobutyl vinyl ether: this monomer was polymerized in dry hexane according to the method of example 17. The polymer was terminated using aqueous ammonium hydroxide solution, precipitated from methanol, filtered, and dried in vacuo. The results are summarized in Table 3.

TABLE 3

| Initiator | [Initiator] mol/ $1 \times 10^3$ | Temp. °C. | Time (hr) | % Yield |
|---|---|---|---|---|
| $(CH_3CH_2)_3O^+$ $(CF_3SO_3)_4Al^-$ | 5.7 | −78 | 0.5 | 96 |
| $(CH_3CH_2)_3O^+$ $(CF_3SO_3)_4Ga^-$ | 2.2 | −78 | 0.5 | 92 |
| $CH_3(C=O)^+$ $(CF_3SO_3)_4B^-$ | 6.1 | −78 | 0.25 | 91 |

EXAMPLE 19

Polymerization of 2-ethyloxazoline: freshly distilled 2-ethyloxazoline, 15 g (0.15 mol), was placed in a dry 100 ml Schlenk flask and the system was evacuated. Dry argon was introduced followed by addition of 70 mg triethyloxonium tetrakis(trifluoromethanesulfonato)aluminate under argon at room temperature. The argon in the flask was evacuated and the flask and contents were allowed to stand for 10 days at which time a completely gelled material was obtained. The reactions was terminated with water and the polymer was subsequently dissolved in acetonitrile and precipitated with ether. The precipitated polymer was isolated by filtration and drying in vacuo, 82% yield. Polymerization with the corresponding tetrakis(trifluoromethanesulfonato)gallate was similarly carried out, 71% yield.

EXAMPLE 20

Polymerization of hexamethyltrisiloxane (hereinafter referred to as "$D_3$"): triethyloxonium tetrakis(trifluoromethanesulfonato)aluminate, 77 mg, was added to a solution of 5 g freshly sublimed $D_3$ in freshly distilled methylene chloride (dried over $P_2O_5$). The viscous material was dissolved in hexane and polydimethylsiloxane was precipitated from pyridine, filtered, and dried in vacuo for 24 hr, 82% yield.

EXAMPLE 21

Polymerization of 1,3-dioxane: A jacketed tube equipped with a magnetic stirrer and argon inlet tube was charged with 5.8 g (65 mmol) freshly distilled 1,3-dioxane and 14 ml dry nitromethane. The system was freeze-thaw degassed and 80 mg triethyloxonium tetrakis(trifluoromethanesulfonato)aluminate was added under argon at −15° C. and the reaction was allowed to continue for 15 hr. The polymerization was quenched by addition of a 5-fold excess (based on initiator) of sodium ethoxide in methanol. The resulting polymer was purified by dissolving it in tetrahydrofuran, precipitation with petroleum ether, filtration, and drying in vacuo, 62 yield. Polymerization with triethyloxonium tetrakis(trifluoromethanesulfonato)gallate was similarly carried out in 37% yield.

EXAMPLE 22

Polymerization of 7-oxabicyclo[2.2.1]heptane (1,4-epoxycyclohexane): a solution of 5.6 g (57 mmol) freshly distilled 1,4-epoxycyclohexane in 16 ml dry dichloromethane contained in a jacketed tube was cooled to 0° C. Triethyloxonium tetrakis(trifluoromethanesulfonato)aluminate, 100 mg, was added under argon. The reaction was allowed to continue at this temperature for 5 days. The resulting polymer was isolated by filtration and dried in vacuo, 73% yield. Polymerization with triethyloxonium tetrakis(trifluoromethanesulfonato)gallate was similarly carried out in 46% yield.

EXAMPLE 23

Preparation of pentakis(trifluoromethanesulfonato)niobium: 5.6 ml trifluoromethanesulfonic acid was added dropwise to 3.4 g (12.5 mmol) niobium pentachloride in 40 ml dry 1,1,2-trichlorotrifluoroethane TM under argon. The mixture was refluxed for 4 days. Removal of the solvent in vacuo gave pentakis(trifluoromethanesulfonato)niobium as a white powder.

Preparation of triethyloxonium hexakis(trifluoromethanesulfonato)niobate: 1.8 g (2.1 mmol) pentakis(trifluoromethanesulfonato)niobium, prepared above, was added to 20 ml dry ether. Ethyl trifluoromethanesulfonate (1.1 g, 6.3 mmol) was added with stirring under dry argon. The mixture was slowly refluxed for 10 hr. The solvent and unreacted ethyl trifluoromethanesulfonate were removed in vacuo to give triethyloxonium hexakis(trifluoromethanesulfonato)niobate as a white solid, 87% yield.

The material obtained above was used to initiate polymerization of tetrahydrofuran according to the procedure of example 14 (9 g tetrahydrofuran, 82 mg triethyloxonium hexakis(trifluoromethanesulfonato)niobate, 14 hr) to give 8.2 g of polytetramethylene ether, 68% isolated yield.

EXAMPLE 24

This example describes the preparation of triethyloxonium hexakis(trifluoromethanesulfonato)tantalate.

Preparation of pentakis(trifluoromethanesulfonato)tantalum: 2.9 ml (33 mmole) trifluoromethanesulfonic acid was added dropwise to 2.3 g (6.4 mmol) tantalum pentachloride in 30 ml dry Freon TM-113. The mixture was refluxed for 7 days. The solvent was removed in vacuo to give pentakis(trifluoromethanesulfonato)tantalum as an off white viscous resin.

Preparation of triethyloxonium hexakis(trifluoromethanesulfonato)tantalate (1-): 0.6 g (3.3 mmol) ethyl trifluoromethanesulfonate was added to 2.1 g (2.2 mmol) pentakis(trifluoromethanesulfonato)tantalum, prepared above, in 25 ml dry ether under argon. The mixture was slowly refluxed for 10 hr. The lower phase which formed was washed several times with dry ether, and dried in vacuo to obtain triethyloxonium hexakis(trifluoromethanesulfonato)tantalate (1-) in 83% yield.

This material was used to polymerize tetrahydrofuran according to the procedure of example 14 (10 g tetrahydrofuran, 6.0 mg triethyloxonium hexakis(trifluoromethanesulfonato)tantalate, 12 hr) to give 6.3 g of polytetramethylene ether, 63% yield.

EXAMPLE 25

This example describes the polymerization of cyclohexene oxide with diphenyliodonium tetrakis(trifluoromethanesulfonato)ferrate (1-): a solution of 3 ml cyclohexene oxide in 3 ml dry dichloromethane containing 30 mg iodonium salt was subjected to irradiation with a medium pressure Hg lamp (Hanovia, 450 W, distance of 2 cm) for 15 min. The colored gelled material was cooled and diluted in tetrahydrofuran. Polycyclohexene oxide was precipitated by addition to methanol and dried in vacuo, 65% isolate yield.

The procedure was performed again in 3 ml acetonitrile as solvent (60 min exposure) to give 36% isolated yield.

The procedure was performed again without solvent (15 min exposure) to give 82% isolated yield.

EXAMPLE 26

This example describes the preparation of triphenylsulfonium tetrakis(trifluoromethanesulfonato)ferrate (1-): 1.4 g (8.7 mmol) ferric chloride was added to a suspension of 2.6 g (8.7 mmol) triphenylsulphonium chloride in 15 ml dry 1,1,2-trichlorotrifluoroethane TM. The mixture was refluxed for 1 hr to give a gray solid precipitate. Dropwise addition of 3.1 ml (34.8 mmol) trifluoromethanesulfonic acid was followed by heating the mixture to reflux for 6 hr. The solvent was removed under reduced pressure and 20 ml dry nitromethane was added. The solution was dried (and residual acid removed) over 0.5 g anhydrous sodium sulfate and 0.2 g sodium bicarbonate. The supernatant liquid was filtered and the solvent removed under reduced pressure to obtain triphenylsulfonium tetrakis(trifluoromethanesulfonato)ferrate (1-) as an off-white solid, 6.7 g (87% yield).

According to the procedure of example 25, 20 mg triphenylsulfonium tetrakis(trifluoromethanesulfonato)ferrate (1-) and 4 ml cyclohexene oxide were irradiated for 10 min to give polycyclohexene oxide, 3.2 g (83% yield).

EXAMPLE 27

This example demonstrates that oxonium salts of the present invention polymerize tetrahydrofuran result in high molecular weight polymers.

Tetrahydrofuran was bulk polymerized with triethyloxonium salts according to the procedure described in example 14 to give polytetramethylene ether. The results are shown in Table 4.

TABLE 4

| Initiator | [Initiator] mol $1 \times 10^{-3}$ | Polytetramethylene Ether $\overline{M}_w \times 10^{-5}$ | $\overline{M}_n \times 10^{-5}$ |
|---|---|---|---|
| $(C_2H_5)_3O^+$ $Al(O_3SCF_3)_4^-$ | 4.8 | 6.85 | 3.42 |
| $(C_2H_5)_3O^+$ $Ta(O_3SCF_3)_4^-$ | 5.3 | 6.35 | 2.77 |

EXAMPLE 28

This example provides a comparison of high molecular weight polytetramethylene ether prepared using the onium salts of the present invention with those prepared according to corresponding prior art methods. Tetrahydrofuran was polymerized according to the method of Rozenberg et al. *Polym. Sci. USSR* 1964, 6, 2246 and Yamashita et al. *Die Makro. Chemie* 1971, 142, 171. The results are presented in Table 5.

TABLE 5

| Oxonium Salt | Polytetramethylene Ether | | | |
|---|---|---|---|---|
| | Solvent | Temp °C. | $\overline{M}_w \times 10^{-5}$ | $\overline{M}_n \times 10^{-5}$ |
| $(C_2H_5)_3O^+$ $BF_4^-$ | ether | 25 | 0.92 | not measured |
| $(C_2H_5)_3O^+$ $Al(O_3SCF_3)_4^-$ | ether | 25 | 1.66 | 0.99 |
| $(C_2H_5)_3O^+$ $Ga(O_3SCF_3)_4^-$ | ether | 25 | 2.82 | 1.48 |
| $(C_2H_5)_3O^+$ $PF_6^-$ | $CH_2Cl_2$ | 0 | not measured | 0.05 |
| $(C_2H_5)_3O^+$ $Al(O_3SCF_3)_4^-$ | $CH_2Cl_2$ | 0 | 0.97 | 0.67 |
| $(C_2H_5)_3O^+$ $Ga(O_3SCF_3)_4^-$ | $CH_2Cl_2$ | 0 | 1.14 | 0.75 |

The above data indicate that the use of the inventive polymerization initiators produces polymers with greater molecular weights as compared to non-inventive or conventional initiators, i.e., $(C_2H_5)_3BF^-_4$ and $(C_2H_5)_3O^+PF^-_6$.

EXAMPLE 29

This example illustrates that anions of the present invention, which have extended chain perfluorosulfonato groups on the metal of the anion, are also useful.

Preparation of tris(perfluorobutanesulfonato)aluminum: to a suspension of 91 g Gramstad, T. *J. Chem. Soc.* 1956, 173) in 30 ml dry 1,1,2-trichlorotrifluoroethane, 0.7 g (10.1 mmole) trimethylaluminum in hexane was added dropwise under dry argon. The mixture was refluxed for 24 hrs. The product was vacuum filtered and washed several times with dry 1,1,2-trichlorotrifluoroethane and finally dried in vacuo to obtain tris(perfluorobutanesulfonato)aluminum as a white powder, 89 g (95% yield).

Preparation of tris(perfluorobutanesulfonato)aluminum: 3 g, (3.2 mol), prepared according to Haszeldine, R. N.; Gramstad, T. *J. Chem. Soc.* 1956, 173), was suspended in dry ether and 3 equivalents of epichlorohydrin were added under dry argon. The mixture was refluxed for 24 hr. The precipitated solid was washed several times with dry ether and finally dried in vacuo to give tetrakis(perfluorobutanesulfonato)aluminate (1-) in 78% yield.

Tetrahydrofuran was bulk polymerized according to example 14 (20 g tetrahydrofuran, 200 mg tetradis(perfluorobutanesulfonato)aluminate (1-), 25 hr reaction), to give a 52% yield of polytetramethylene ether.

EXAMPLE 30

This example demonstrates the preparation of triethyloxonium hexakis(trifluoromethanesulfonato)zirconate (2-).

Ethyl trifluoromethanesulfonate (1.2 g, 6.6 mmol) was added to a solution of 1.5 g (2.1 mmol) tetrakis(trifluoromethanesulfonato)zirconium prepared according to the procedure of Schmeiber, M.; Sartaori, P.; Lippsmeier, B. *Chem. Ber.* 1970, 103, 868, in 20 ml dry ether under argon. The mixture was slowly refluxed for 10 hr, and the precipitated solid was washed several times with dry ether and finally dried in vacuo at 40° C. for 2 hr to give triethyloxonium hexakis(trifluoromethanesulfonato)zirconate (2-) in 89% yield.

This material was used to polymerize tetrahydrofuran and cyclohexene oxide according to examples 14 and 15, respectively. In the case of tetrahydrofuran (10 g tetrahydrofuran, 67 mg triethyloxonium hexakis(trifluoromethanesulfonato)zirconate (2-), 14 hr) a 58% yield was obtained, while in the latter case (2 g cyclohexene oxide, 2 g dichloromethane, 2° C., 10 min), a 70% yield was obtained.

EXAMPLE 31

Acetylium hexakis(trifluoromethanesulfonato)niobate (1-) was prepared according to the procedure of example 10 in 88% yield. The salt thus prepared was used to polymerize tetrahydrofuran and cyclohexene according to the procedure of examples 14 and 15 in 54% (12 hr, 25° C.) and 61% (15 min, 0° C.) yields, respectively.

As can be seen from these examples, the synthesis of all compounds within the scope of the invention can be performed by selecting the appropriate reagents and using the teachings of this specification and the reference materials cited.

I claim:

1. A process for the polymerization of a cationically polymerizable monomer comprising intimately contacting a cationically polymerizable monomer with a cationic polymerization initiator thereby initiating polymerization of said monomer, said initiator being represented by the following formula:

$$Y_a^{b+}[(RSO_3)_nM)]^{Z-}$$

wherein:

Y is a cation selected from the group consisting of oxonium, sulfonium, sulfoxonium, selenonium, iodonium, diazonium, pyrylium, carbenium, and acylium cations;

R is independently selected from the group consisting of

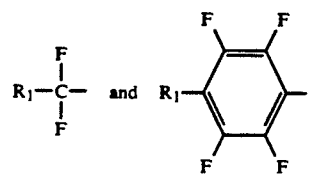

$R_1$ is hydrogen, halogen, an alkyl group or an aryl group;

F is fluorine;

M is an element chosen from Groups 3-15, inclusive, of the Periodic Table;

z is 1, 2, 3, or 4; and a, b, and n are integers such that z is less than or equal to n and the product of a multiplied by b equals z.

2. A process as recited in claim 1 wherein said monomer is one which is capable of being polymerized cationically through initiation with an alkyl group or an aryl group containing cation.

3. A process as recited in claim 1 wherein said monomer is one selected from the group consisting of epoxides, oxetanes, tetrahydrofurans, tetrahydropyrans, vinyls, lactones, oxazolines, aziridines, cyclosiloxanes, ketals, cyclic anhydrides, lactams, and α-phthalaldehydes.

4. A process as recited it claim 1 wherein the contacting of said monomer and said initiator is carried out in solution.

5. A process as recited it claim 1 wherein said polymerization reaction is carried out under anhydrous conditions.

6. A process as recited it claim 1 wherein at least one alkyl group of aryl group is attached to the cation Y.

7. A process as recited it claim 1 wherein Y is an oxonium cation.

8. A process as recited it claim 1 wherein M is an element selected from Groups 4-14, inclusive, of the Periodic Table.

9. A process as recited it claim 8 wherein M is an element selected from B, Al, Ga, Sn, Fe, Zr, Hf, Nb, and Ta.

10. A process as recited it claim 1 wherein each R individually represents a perfluorinated alkyl radical or aryl radical.

11. A process as recited it claim 10 wherein R is each R is individually a $C_1$-$C_{10}$ perfluorinated alkyl radical.

* * * * *